US006866410B2

(12) United States Patent
Jesurun et al.

(10) Patent No.: US 6,866,410 B2
(45) Date of Patent: Mar. 15, 2005

(54) AMBIENT LIGHTING SYSTEM FOR SURGICAL LIGHTS

(75) Inventors: David Jesurun, S. Euclid, OH (US); Allan J. Greszler, Elyria, OH (US); Yury Keselman, Beachwood, OH (US)

(73) Assignee: Steris, Inc., Temecula, CA (US)

( * ) Notice: Subject to any disclaimer, the term of this patent is extended or adjusted under 35 U.S.C. 154(b) by 0 days.

(21) Appl. No.: 10/374,880

(22) Filed: Feb. 25, 2003

(65) Prior Publication Data

US 2003/0161152 A1 Aug. 28, 2003

Related U.S. Application Data

(60) Provisional application No. 60/359,516, filed on Feb. 25, 2002.

(51) Int. Cl.[7] ............................ A61B 1/06; F21V 21/26

(52) U.S. Cl. ........................ 362/572; 362/250; 362/225; 362/804

(58) Field of Search ................................ 362/250, 225, 362/33, 572, 573, 804, 236, 237, 554, 556, 555, 576, 581, 551, 404, 405, 406, 408; 600/249; 606/10; 607/88, 90, 91, 93

(56) References Cited

U.S. PATENT DOCUMENTS

| | | | | |
|---|---|---|---|---|
| 2,069,816 A | | 2/1937 | Child | 62/288 |
| 2,173,325 A | * | 9/1939 | Alexander | 362/33 |
| 2,297,781 A | | 10/1942 | Korengold | 362/280 |
| 2,896,066 A | | 7/1959 | Quetin | 362/33 |
| 3,360,640 A | | 12/1967 | Seitz et al. | 362/12 |
| 3,428,797 A | | 2/1969 | Haynes | 362/572 |
| 3,928,757 A | | 12/1975 | Nelson | 362/228 |
| 4,234,907 A | | 11/1980 | Daniel | 362/556 |
| 4,280,167 A | * | 7/1981 | Ellett | 362/33 |
| 4,581,689 A | | 4/1986 | Oram | 362/275 |
| 4,761,047 A | | 8/1988 | Mori | 607/88 |
| 5,117,340 A | | 5/1992 | Schäfer | 362/148 |
| 5,165,786 A | | 11/1992 | Hubert | 362/287 |
| 5,339,223 A | | 8/1994 | Kremenchugsky et al. | 362/572 |
| 5,383,105 A | | 1/1995 | Agut | 362/285 |
| 5,539,626 A | | 7/1996 | Scholz | 362/249 |
| 6,132,062 A | | 10/2000 | Borders et al. | 362/251 |
| 6,155,693 A | | 12/2000 | Spiegel et al. | 362/147 |
| 6,461,032 B2 | * | 10/2002 | McKinley | 362/555 |
| 6,464,383 B1 | * | 10/2002 | Northington et al. | 362/572 |
| 6,601,985 B1 | * | 8/2003 | Jesurun et al. | 362/572 |
| 6,639,623 B2 | * | 10/2003 | Howell et al. | 362/11 |

FOREIGN PATENT DOCUMENTS

| | | |
|---|---|---|
| DE | 43 35 254 A1 | 10/1993 |
| FR | 2395460 | 6/1978 |
| FR | 2775515 | 2/1998 |

* cited by examiner

*Primary Examiner*—Thomas M. Sember
*Assistant Examiner*—Bao Q. Truong
(74) *Attorney, Agent, or Firm*—Fay, Sharpe, Fagan, Minnich & McKee, LLP

(57) ABSTRACT

A lighting system (10) suited to use in an operating theater includes one or more lightheads (14, 16), and an ambient lighting system (28) having one or more light emitting components (60). The light emitting components are mounted within a canopy assembly (49) of the lighthead and arranged around a central support hub (33) to provide even illumination throughout the room. The canopy assembly includes a canopy and a canopy extension (70, 70'), which is removably mounted to the canopy, allowing the ambient lighting system to be retrofitted to an existing lighting system.

26 Claims, 11 Drawing Sheets

AMBIENT LIGHTING SYSTEM FOR SURGICAL LIGHTS

This application claims the priority of U.S. Provisional Application Ser. No. 60/359,516, filed Feb. 25, 2002.

BACKGROUND OF THE INVENTION

The present invention relates to the surgical lighting arts. It finds particular application in conjunction with providing ambient lighting for use in operating room (OR) settings and will be described with particular reference thereto. It is to be appreciated, however, that the invention also finds application in conjunction with providing soft, uniformly distributed ambient lighting in other settings and applications and is not limited to the aforementioned surgical lighting embodiment.

Typically, in an operating room setting, large, high lumen output lightheads are used to illuminate the surgical site. One or more lightheads are suspended on articulated arms connected to the structural ceiling above the surgical table. Additionally, ambient lighting is often employed in the room during certain procedures where the larger lightheads are to be switched off so that the surgeons, nurses, and other support staff can observe video monitors and the like without the glare induced by the surgical lightheads. The ambient lighting enables the personnel to see and move about in regions of the room apart from the operating table.

In some present OR lighting systems, smaller lights are mounted on the upper portions of the surgical lighthead support arms to provide ambient lighting. However, systems of this type typically do not lend themselves well to ambient lighting for surgical applications because the light is usually directed at the ceiling or wall resulting in a non-uniform distribution of light throughout the room. Being largely directional in nature, these lights tend to illuminate some areas of the room, while leaving other portions of the room in darkness. Also, directional light can be inadvertently positioned in such a manner as to disrupt the vision of surgeons, nurses, or anesthetists. Further, the lighthead may need to be moved during a procedure, requiring a non-sterile nurse to move the lighthead, consuming both the nurse's time, and the surgeon's time.

The present invention provides a new and improved ambient lighting method and apparatus that overcomes the above-referenced problems and others to generate a soft, uniformly distributed ambient light that is particularly useful in surgical operating room applications.

SUMMARY OF THE INVENTION

According to one aspect of the invention, a lighting system is provided. The system includes a support hub and a lighthead including a first light emitting component. An arm assembly is adapted to support the lighthead in a selected position relative to the support hub. An ambient light includes a second light emitting component, the light emitting component is carried by the support hub and is spaced from the arm assembly.

In accordance with another aspect of the present invention, a medical device suspension system is provided. The system includes a support tube. An arm assembly is mounted for rotational movement of the arm assembly relative to the support tube by a spindle. The arm assembly supports an associated medical device at a distal end thereof. A canopy assembly is mounted to the tube above the spindle. At least a light emitting portion of an ambient light is mounted to the canopy assembly adjacent its periphery.

In accordance with another aspect of the present invention, a method of fitting an ambient light to a medical suspension system is provided. The method includes mounting a canopy extension to a canopy of the suspension system. The canopy extension supports, at least in part, a light emitting portion of the ambient light.

One advantage of at least one embodiment of the present invention is the provision of a diffuse ambient lighting system.

Another advantage of at least one embodiment of the present invention is that the ambient light remains stationary, even when the lightheads are repositioned.

Another advantage of at least one embodiment of the present invention is that the ambient light may be retrofitted to an existing light system.

Still further advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
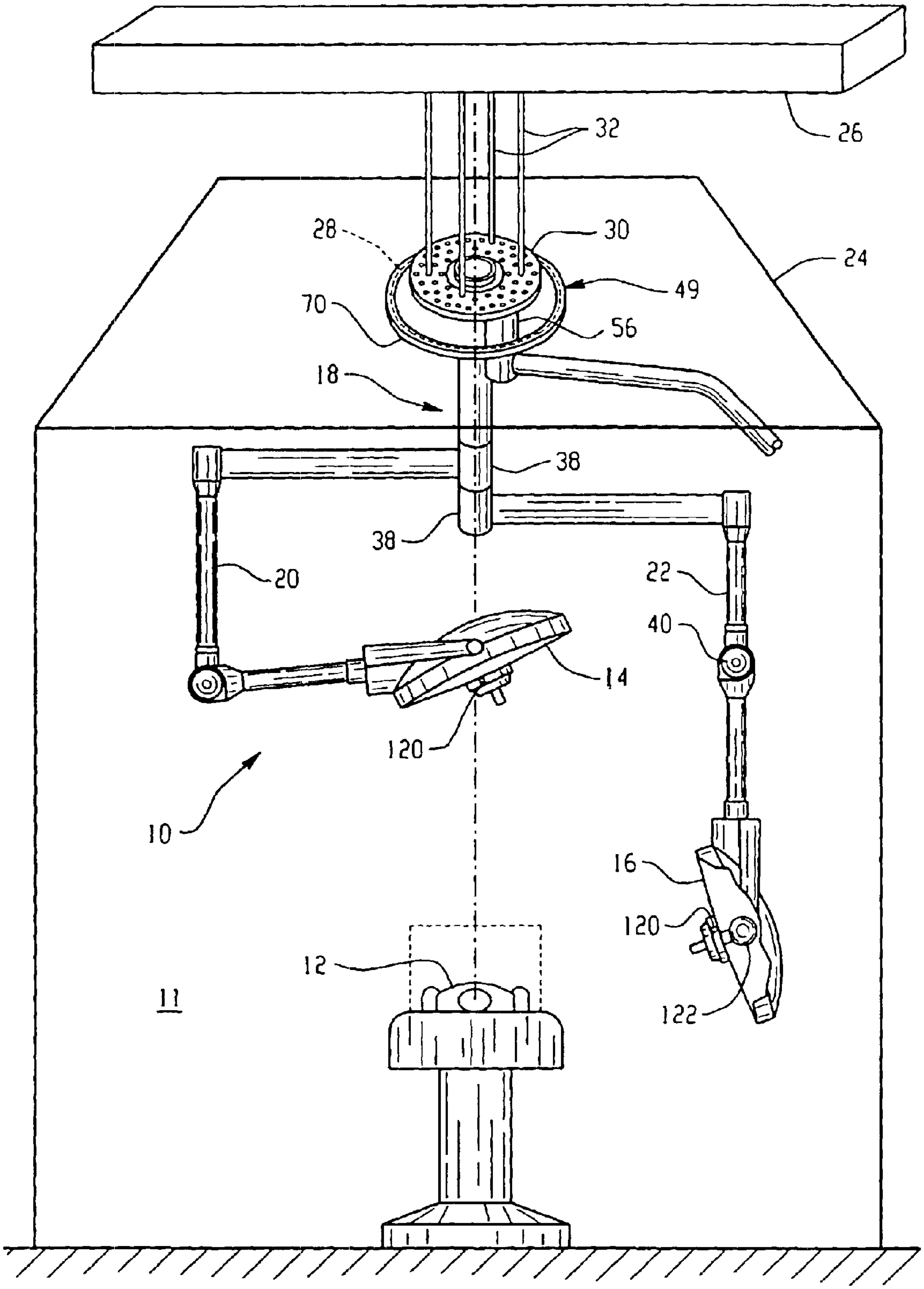
FIG. 1 is a perspective view of a lighting system including a canopy assembly in accordance with the invention.

With reference to FIG. 1, an overhead lighting system 10 suited to use in an operating room 11 illuminates areas of a patient 12 undergoing surgery and provides ambient light for general room illumination. The system 10 illustrated in FIG. 1 includes two lightheads 14, 16, which are suspended from a common mounting system 18 by articulated arm assemblies 20, 22, respectively. The arm assemblies allow the lightheads 14, 16 to be independently movable to a variety of positions relative to a ceiling 24 and the patient 12. The lighting system 10 is rigidly mounted to a suitable stationary support 26, such as a beam, typically located above the ceiling 24. The lightheads 14, 16 provide directional light, which is focused on the patient or other desired location. The lighting system also includes an ambient light 28, which provides a diffuse, generally non-directional illumination of the operating room, particularly for use when the lightheads 14, 16 are switched off or set to a low illumination level. The ambient light includes one or more light emitting components, as will be described in greater detail below. As will be appreciated, the lighting system 10 may alternatively or additionally include other medical devices, such as task lights, monitors, cameras, and the like, which are mounted to the mounting system by articulated arms analogous to arm assemblies 20, 22.

Figure 2:
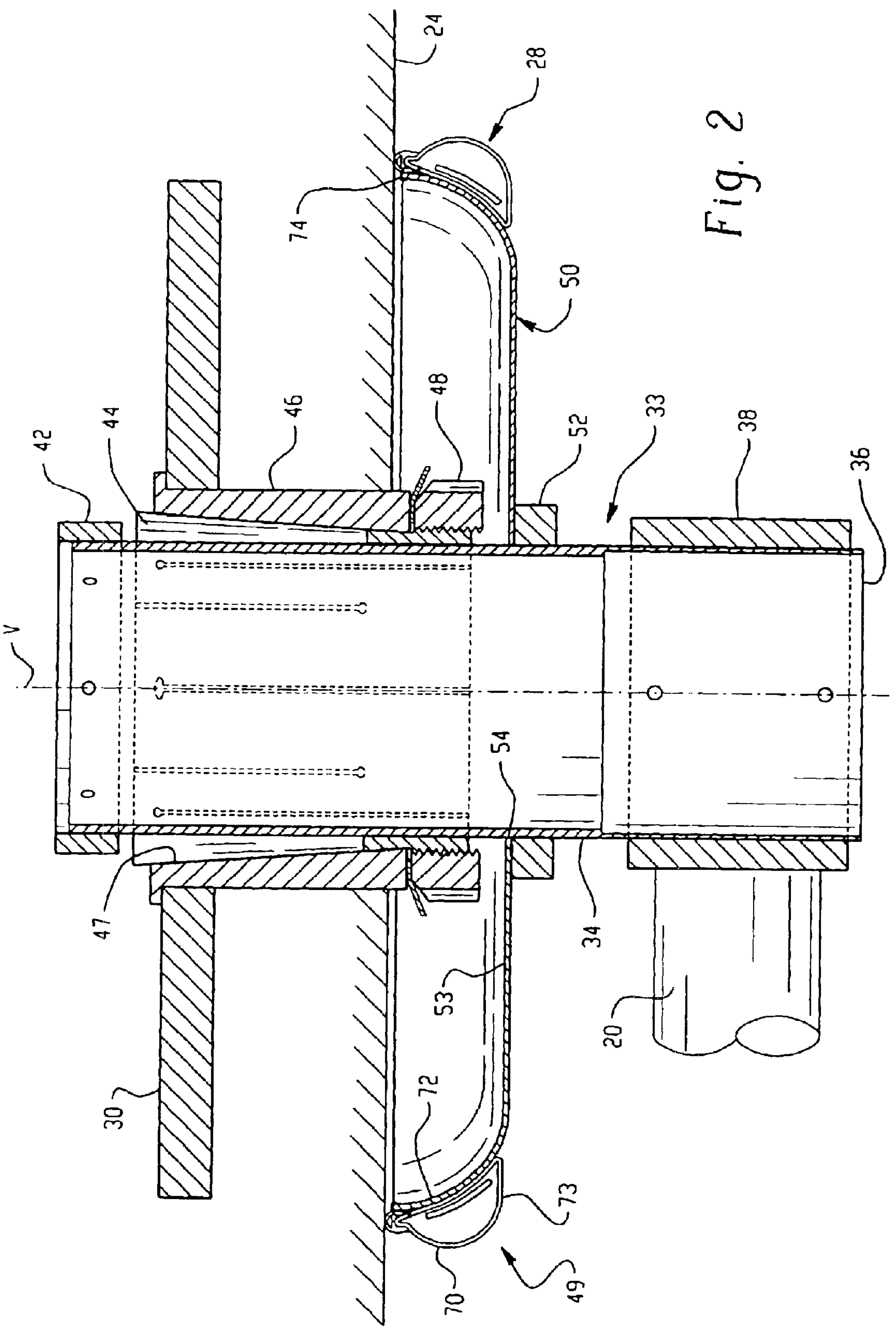
FIG. 2 is an enlarged sectional view of the support hub and canopy assembly of FIG. 1 with a canopy extension according to a first embodiment of the present invention.

With reference also to FIG. 2, the common mounting system 18 includes a circular mounting plate or "cheese-plate" 30, which is attached to the rigid structure 26 by a plurality of long-shank fasteners 32, and a support hub 33. The support hub comprises a hollow, cylindrical support tube or drop tube 34, which is clamped at a proximal end to the mounting plate 30 and has a distal end 36 extending downward. The articulating arm assemblies 20, 22 are each connected to the drop tube distal end 36 by a rotatable hub portion or spindle 38, which is rotatable about a vertical axis V. Each articulating arm 20, 22 usually includes one or multiple joints 40 which are adjustable about one or more axes each to provide additional degrees of motion freedom.

The length of the drop tube 34 extending below the cheeseplate 30 is adjustable, by means of a wedge lock 42. The wedge lock 42 includes a frustoconical collar 44, which is removably received within a similarly shaped weldment 46, rigidly attached to or integrally formed with the cheese-plate 30. The weldment 46 has a central bore 47, which is shaped to receive the drop tube therethrough. A nut 48 is threaded on to a lower end of the collar 44, below the weldment 46, thereby drawing the collar into a clamping relation on the drop tube 34.

Figure 3:
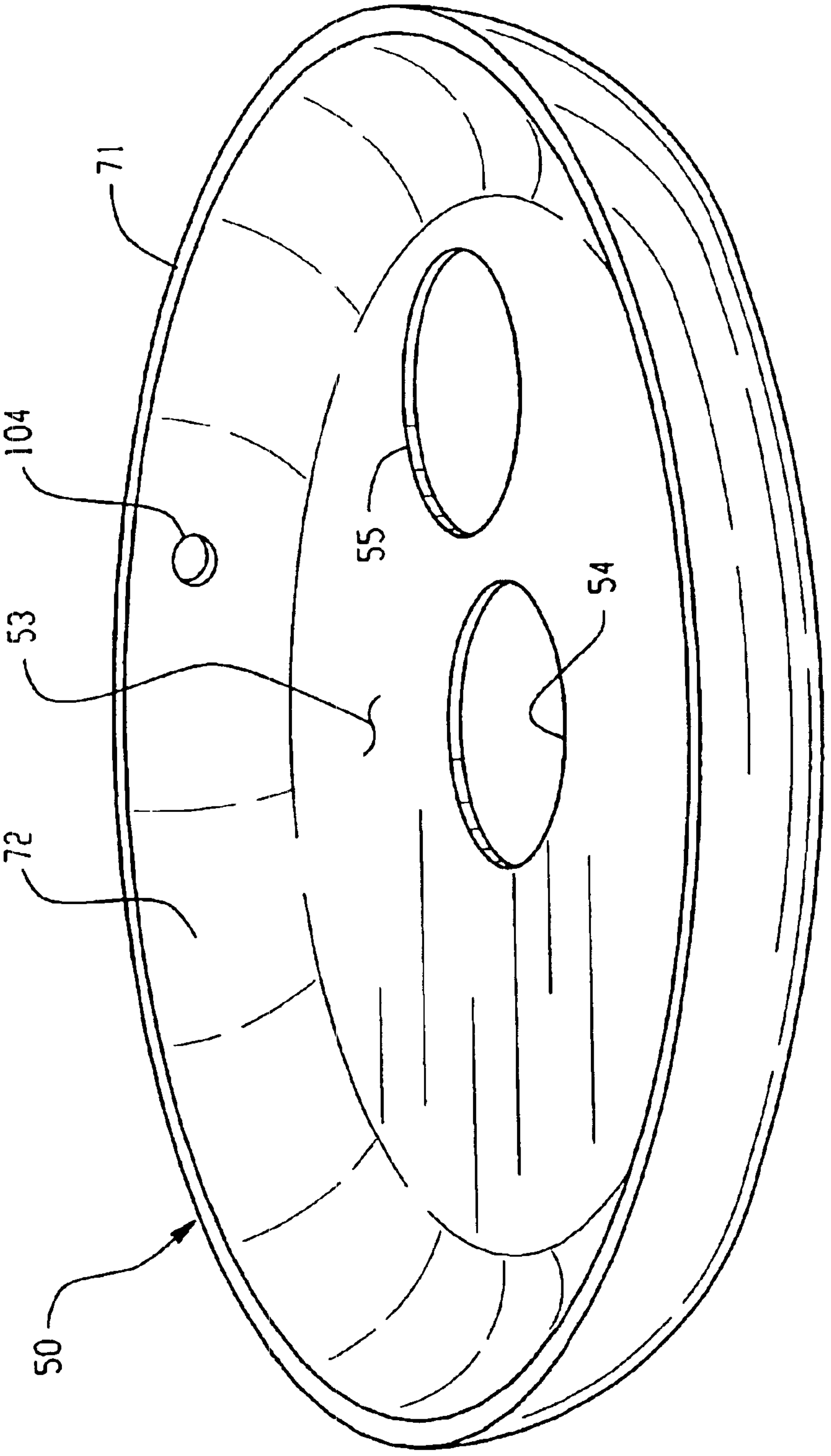
FIG. 3 is an enlarged perspective view of the canopy of FIG. 1.

With continued reference to FIG. 2, a canopy assembly 49 includes a main body in the form of a dome-shaped ceiling cover or canopy 50, which provides a cosmetic cover for the cheeseplate 30 and associated mountings and acts as a support for the ambient light 28. The canopy 50 is mounted to the drop tube 34, below the weldment 46 and nut 48, by a suitable securement member 52. For example, the canopy 50 is clamped to the drop tube by a canopy clamp ring 52. The canopy has a generally horizontally extending base portion 53 with a central aperture 54 wide enough to accommodate the drop tube 34 therethrough. The canopy clamp ring 52 is seated below the canopy adjacent the aperture 54. The canopy, thus mounted, extends radially from the drop tube 34 in an annulus, with the base portion 53 being spaced from the cheeseplate 30 and aligned generally parallel therewith. One or more additional off-center apertures 55 (FIG. 3) are optionally provided in the canopy 50 to accommodate additional auxiliary support hubs 56 (FIG. 1).

Figure 4:
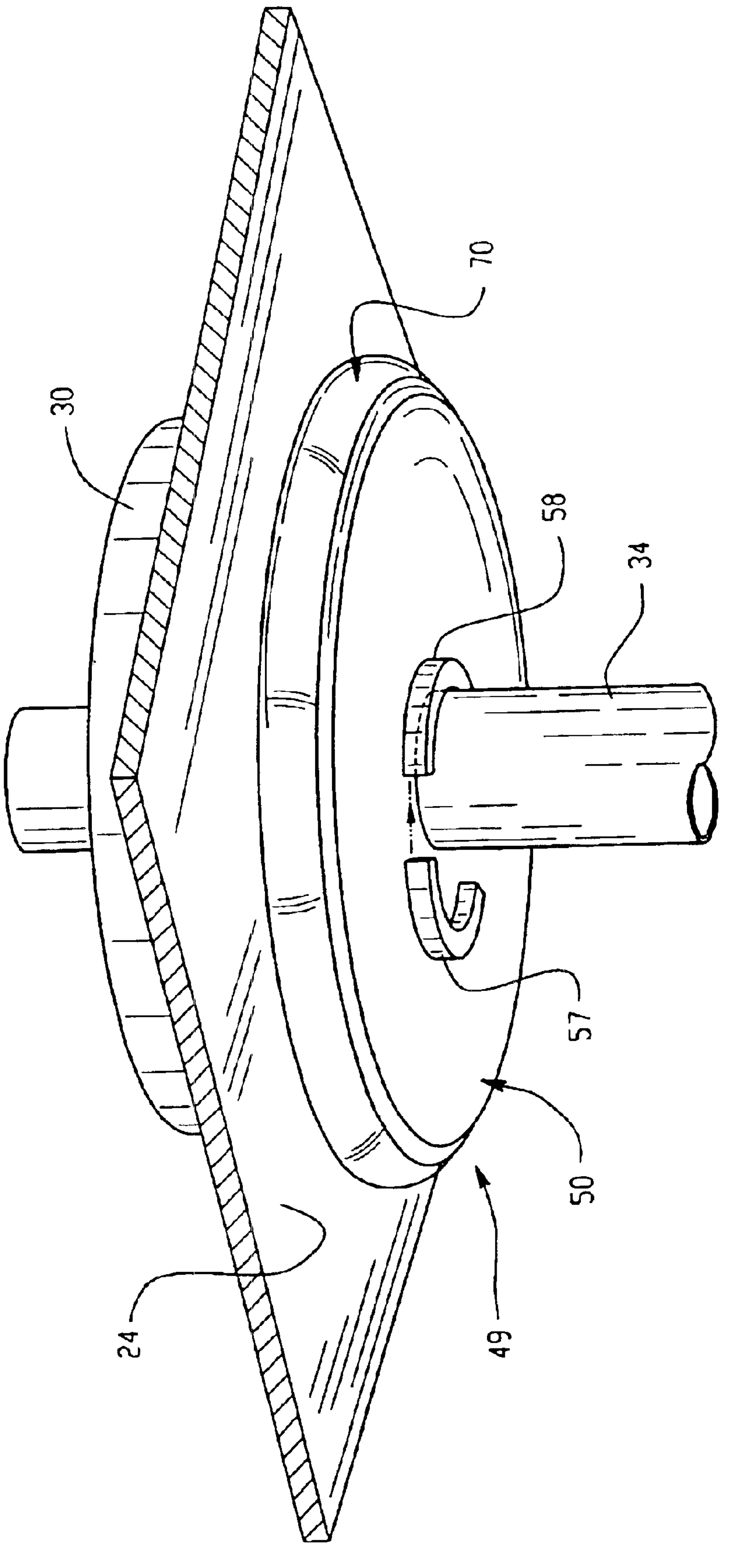
FIG. 4 is an enlarged perspective view from below of the canopy assembly and support hub of FIG. 1, with a clamp ring during assembly.

In one embodiment, best shown in FIG. 4, the securing member 52 is in the form of two half rings 57, 58. The canopy 50 is secured by locking the half-rings 57, 58 together, around the drop tube. Since the canopy 50 does not bear the weight of the arm assemblies 20, 22, the securing does not need to be particularly strong, and various securing components are contemplated in place of the rings 57, 58.

Figure 5:
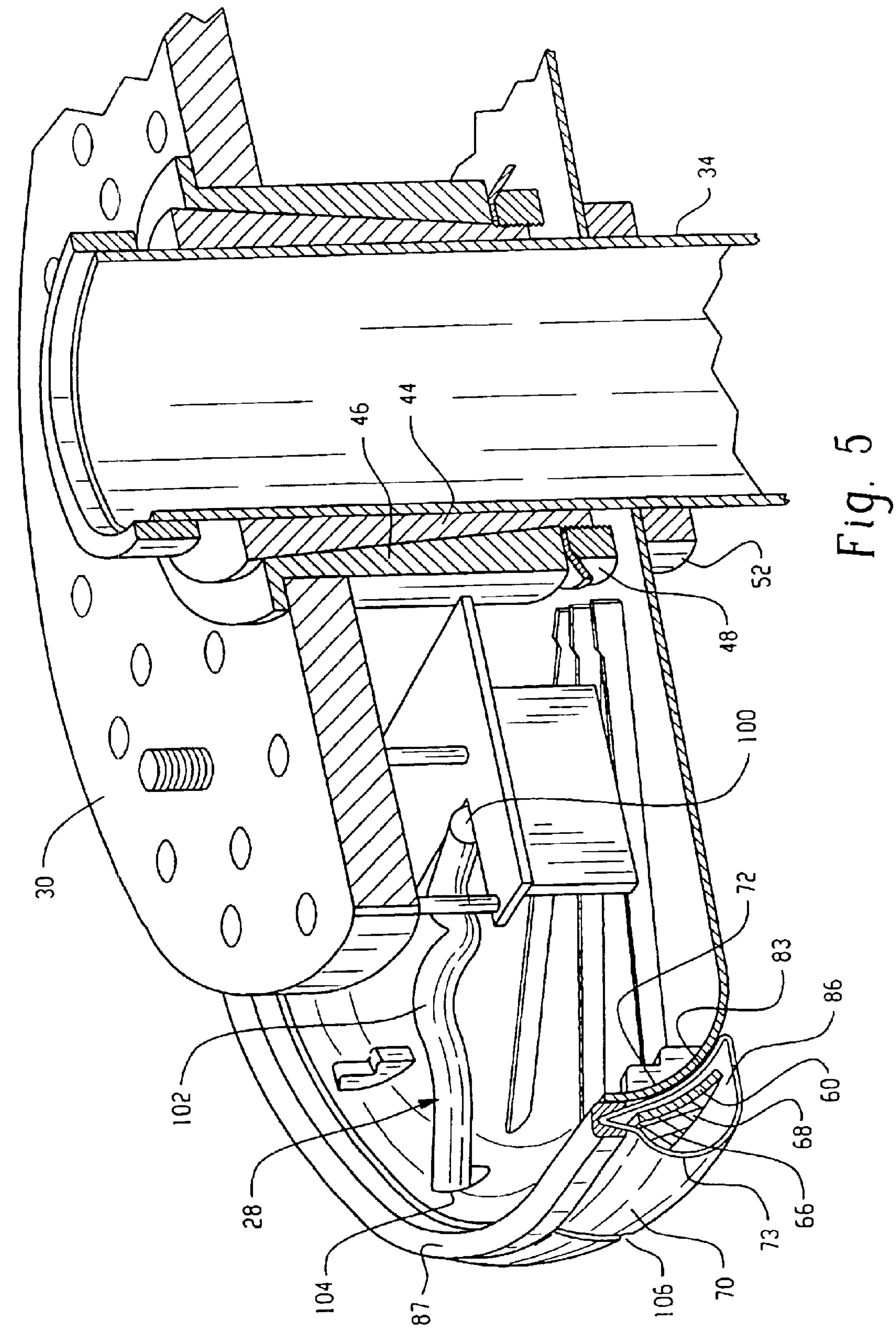
FIG. 5 is a perspective view, in partial section, of the canopy assembly of FIG. 4, with an ambient light according to one embodiment of the invention.
Figure 6:
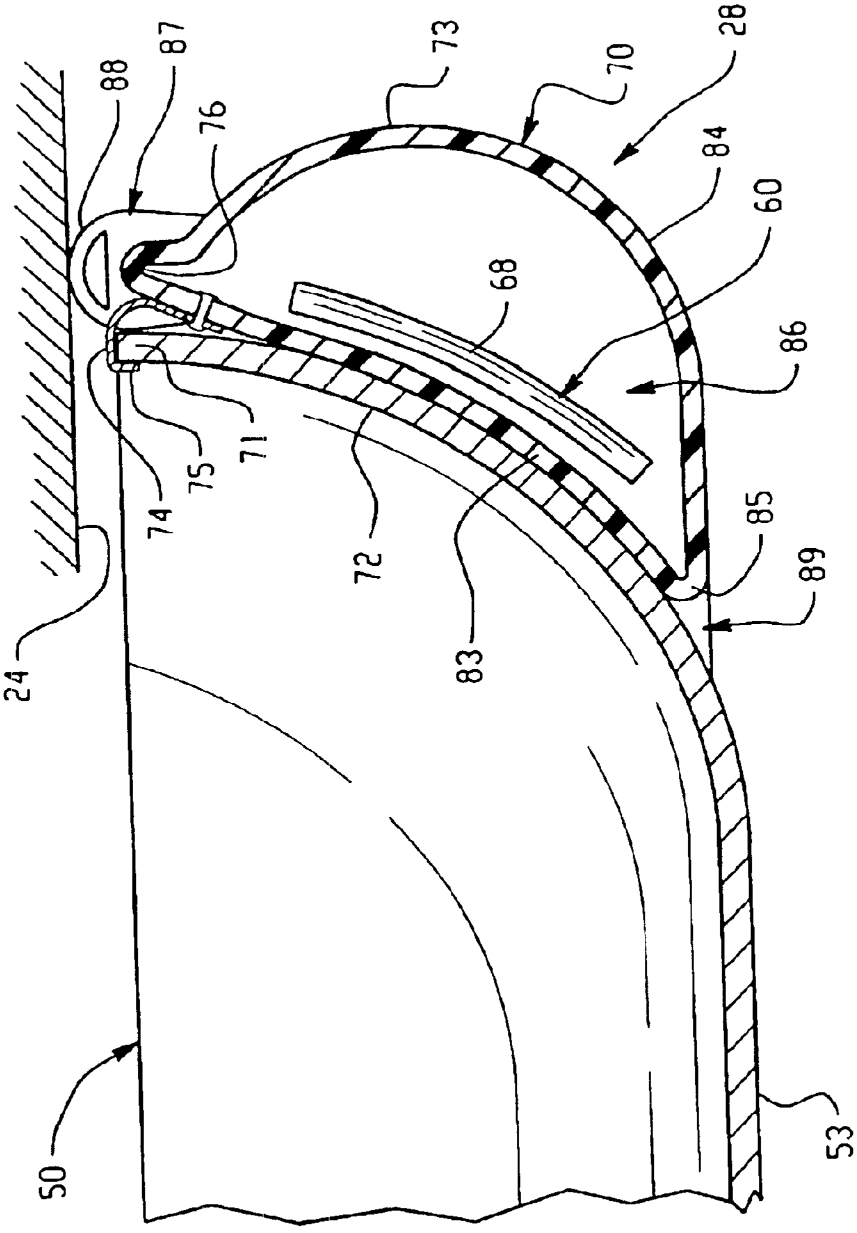
FIG. 6 is an enlarged sectional view of the canopy and canopy extension of FIG. 2.

With reference once more to FIG. 2, and reference also to FIGS. 5 and 6, the ambient light 28 includes at least one light emitting component 60. The ambient light 28 may comprise a single light emitting component 60, such as a fluorescent light, an incandescent lamp, a light emitting diode (LED), a discharge light, or a fiberoptic element. Alternatively, the ambient light 28 includes a plurality of light emitting components 60, such as a plurality of fluorescent lights, incandescent lamps, LEDs, discharge lights, or fiberoptic elements. Preferably, the light emitting component or components are arranged around the drop tube 34, such that a diffuse light is emitted in all angular directions.

FIGS. 5 and 6 show one embodiment of an ambient light 28, in which the light emitting component 60 includes a plurality of fiberoptic cables 66, in the form of a woven mesh 68, arranged in an annulus around the weldment 46 and drop tube (FIG. 2).

In an alternative embodiment (not shown), a generally circular fluorescent light is radially spaced from the drop tube and inscribes an almost complete circle. Operating components for the fluorescent tube, such as electrical connections and/or a ballast, are optionally mounted on the cheeseplate. In another alternative embodiment (not shown), a plurality of fluorescent tubes, which may be arcuately shaped or linear, are arranged in an annulus or approximation thereof.

In yet another alternative embodiment (not shown), the light emitting component includes a matrix of LEDs, arcuately arranged in an annulus around the drop tube.

As best shown in FIGS. 2 and 5, the canopy assembly 49 preferably supports at least the light emitting component 60 of the ambient light 28. Specifically, as shown in FIG. 2, the canopy assembly 49 includes an annular canopy extension 70. By "annular" it is meant for the canopy extension to include both circular bodies as well as elliptical and polygonal bodies, such as hexagons, or octagons, where the body defines an aperture, spaced inward from its peripheral edge, which may be centrally or off-centrally located. Preferably, the canopy extension 70 completely encircles the canopy 50, although it is also contemplated that the canopy extension may only encircle about 70% or more, more preferably, at least 90% of the canopy.

The canopy extension 70 is removably mounted to an upper end 71 of a peripheral edge or upwardly curving lip 72 of the canopy 50. In the illustrated embodiment, an annular housing 73 of the canopy extension 70 is mounted to the lip 72 by fasteners 74. In the embodiment shown in FIG. 6, the fasteners include a plurality of arcuately spaced hooks 75 which engage the lip 72 of the canopy 50. The hooks are mounted to the canopy extension housing 73 at or adjacent an upper end 76 thereof.

Figure 8:
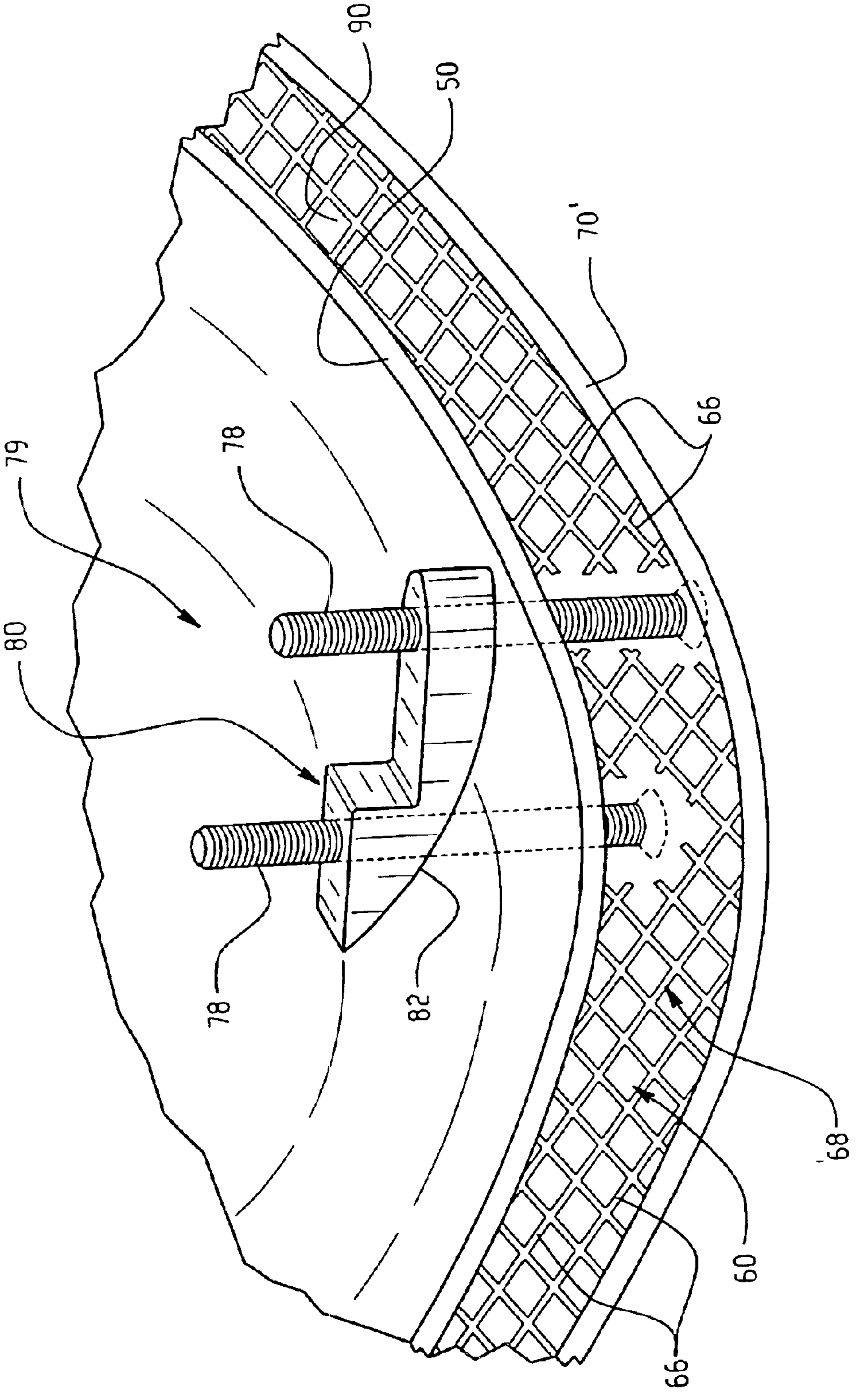
FIG. 8 is an enlarged perspective view from above of the canopy assembly of FIG. 7.
Figure 9:
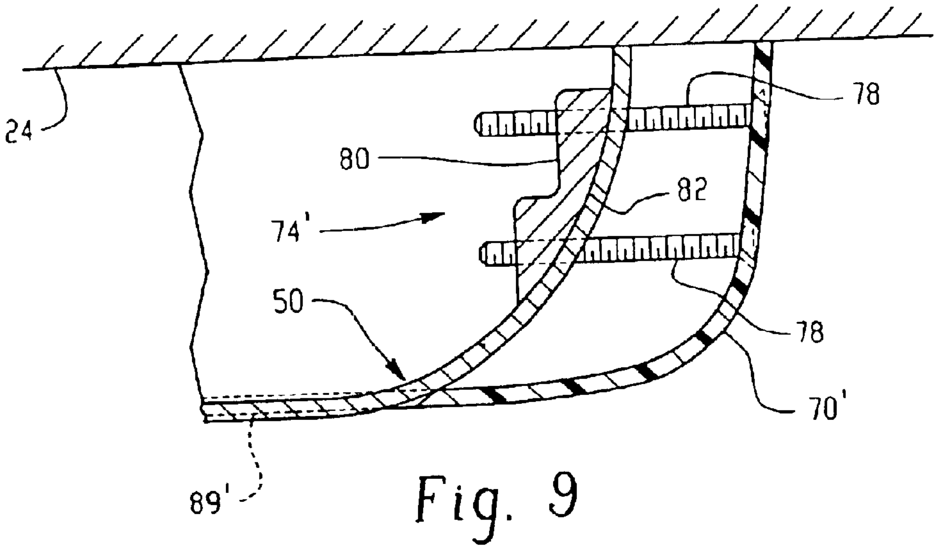
FIG. 9 is an enlarged sectional view of part of the canopy assembly of FIG. 7.

Additional or alternative fasteners are also contemplated. For example, in an alternative embodiment of a canopy extension 70' shown in FIGS. 7–9, where similar elements are denoted with a prime (') and new elements are given new numbers, the fasteners 74' each include bolts, screws, adhesive, or other suitable securement means. In the embodiment illustrated in FIGS. 7-9, a plurality of fasteners 74' is arcuately positioned around the canopy 50. Each fastener 74' includes two bolts 78 that are inserted through holes (not shown) provided in the canopy extension 70' and matching holes (not shown) provided in the canopy 50. Corresponding bores (not shown) in a support member 80 receive the two bolts 78. The support member 80 reinforces the canopy 50 around the provided holes. For this purpose, the support member 80 has a curved surface 82, best shown in FIG. 8, which matches the corresponding adjacent curved surface of the canopy 50. It will be appreciated that bolts 78 and support members 80 as shown in FIG. 8 may also be used for rigidly attaching the canopy extension 70 of FIG. 2 to the canopy 50, either alone or in addition to the hooks 75.

The canopy extension 70, 70' may be a single annular curved body, or may be formed in two or more segments, each defining an arc-shaped portion of the canopy extension, which are secured together to form an annular body during assembly using clamp members, rings, drilling, tapping, or other suitable means. The ambient light 28 can thus be retrofitted onto an existing surgical lighting system 10 without the need for removal of the support hub 33 from the structural ceiling.

As shown in FIG. 6, the annular housing 73 of the canopy extension 70 has a curved inner peripheral wall 83, of the same general curvature as the lip 72 of the canopy, which is seated against the canopy lip, and a bowed outer peripheral wall 84, which meets the inner wall at upper and lower ends 76, 85, thereof to define an enclosed annular cavity or pocket 86 therebetween having a generally crescent-shaped cross section. The light emitting component 68 is sealed within the pocket 86. Thus, all (or substantially all) light from the light emitting component 60 enters the room 11 by passing through the canopy assembly housing 73. A u-shaped rubber gasket 87 grips the upper end 76 of the canopy extension housing 73 between arms of the U. A resiliently flexible cap 88 of the gasket 87 projects above the canopy 50 and canopy extension housing 73 and may engage the ceiling 24 or the cheeseplate 30 in service. The cap 88 thus inhibits damage to the canopy extension 70 during installation or upon slight movement of the canopy assembly 49, such as when the arm assemblies 20, 22 are repositioned.

As can be seen from FIGS. 2 and 6, the canopy extension 70 is of somewhat larger outer diameter than the canopy 50. The peripheral edge 72 of the canopy is thus spaced radially inward of the curved inner wall 83 on the canopy extension housing 73. The canopy extension 70 defines a large central aperture 89, sized to accommodate both the central drop tube 34 and any off-center auxiliary drop tubes 56 therethrough.

Figure 10:
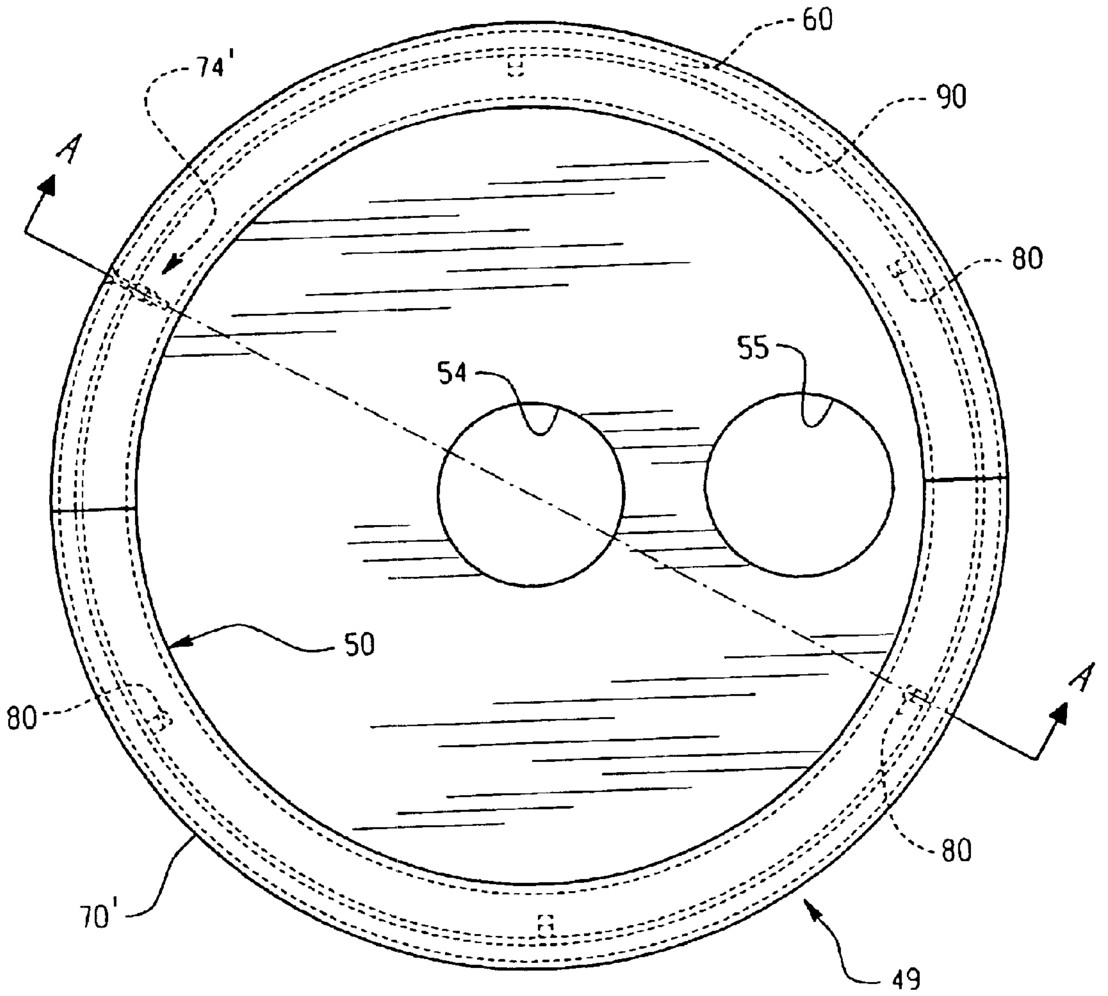
FIG. 10 is an enlarged top view of the canopy assembly of FIG. 7.

In the embodiment of FIGS. 714 10, the canopy extension 70' lacks the inner wall 83 of FIG. 6. Instead, a cavity in the form of a socket 90 with an upward facing opening 92 is defined between the peripheral edge 72 of the canopy and the canopy extension 70'. The socket 90 receives the light emitting component 60 therein, which in the illustrated embodiment, includes a woven mesh 68 of fluorescent tubes. The upper opening 92 is positioned adjacent the ceiling 24, thus creating an essentially enclosed pocket for the light emitting component 60. Thus, substantially all light from the light emitting component 60 enters the room by passing through the canopy extension 70'.

Figure 7:
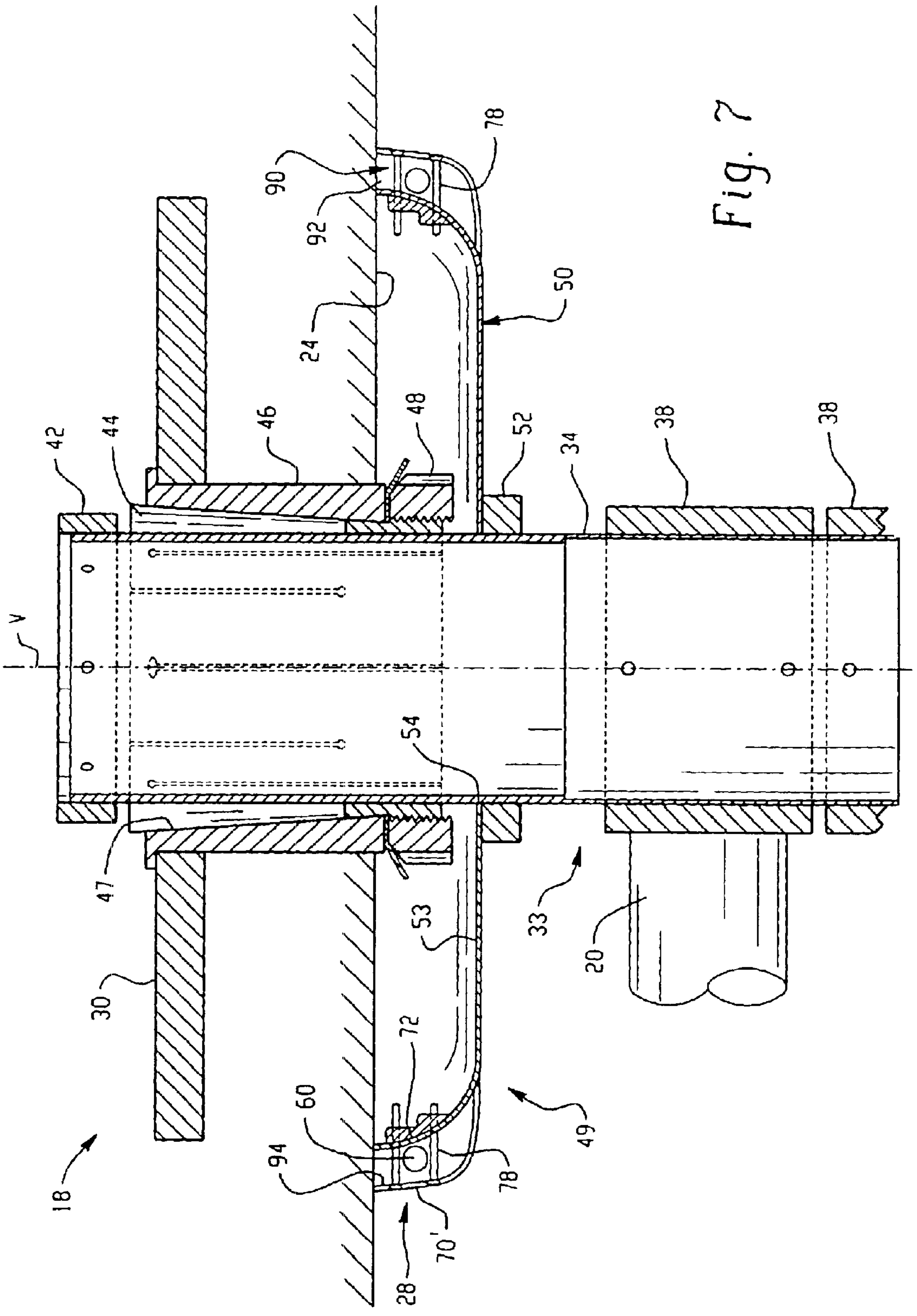
FIG. 7 is an enlarged sectional view of the support hub and canopy of FIG. 1 with a canopy extension according to a second embodiment of the present invention.

As shown in FIG. 7, the canopy extension 70' is of somewhat larger diameter than the canopy 50 and has a peripheral wall in the form of a lip 94 at its outer peripheral edge of somewhat lesser curvature to that of the lip 72 formed by the outer peripheral edge of the canopy. The peripheral edge 72 of the canopy is thus spaced radially inward of the lip 94 on the canopy extension. The canopy extension 70' has a large central aperture 89' (FIG. 9) sized to accommodate both the central drop tube 34 and any off-center auxiliary drop tubes 56 therethrough.

In an alternative embodiment (not shown), the canopy extension is dome shaped, and has a generally circular base portion which engages the corresponding base portion 53 of the canopy. One or more apertures are formed in the canopy extension base portion, similar to apertures 54, 55 in the canopy, which are suitably sized for snugly receiving the central drop tube 34 and any auxiliary tubes 56 therethrough.

In yet another embodiment (not shown), the canopy extension is integrally formed as one piece with the canopy 50.

In a yet still further embodiment (not shown), the canopy and canopy extension are formed in two or more arcuate sections each section comprising an arcuate portion of the canopy and an arcuate portion the canopy extension, integrally formed therewith. The segments are clamped together, by suitable fixing members, such as screws, bolts, or the like, around the drop tube, and then held in vertical position by the clamp rings 57, 58.

The canopy extension 70, 70', or at least the outer peripheral wall 84, 94 thereof, is formed from a transparent or translucent material, which is light transmissive to the light emitted from the light emitting component 60. For example, the canopy extension 70, 70' and optionally also the canopy 50, is formed from a frosted, white or light colored plastic, which diffuses the light passing through it, so that the light is distributed generally uniformly throughout the room.

The location of the light emitting component 60 of the ambient light 28 around and close to the central support tube 34 distributes the ambient light generally uniformly throughout the surgical room. The centralized location of the ring-shaped ambient light emitting component 60 eliminates the need for a non-sterile nurse to manipulate the light 28 or otherwise redirect it during operations, as is the case where an ambient light is mounted to one of the articulating arms, and thus is often moved when the arm is repositioned.

With reference once more to the embodiment of FIGS. 2–6, the light emitting component 60 of the ambient light 28 may be supplied with light from a light source 100, such as an incandescent bulb, LED, or bank of LEDs, which may be spaced from the light emitting component 60. The light source 100 is coupled, through an optical light pipe 102 or bundle of light pipes, to the light emitting component 60. In the illustrated embodiment, the light emitting component 60 is in the form of a light diffuser, such as a woven fiber optic element 68, which is supported within the pocket 86 of the canopy extension 70. One suitable woven fiber optic element 68 is available commercially from Lumitex. The light pipe 102 passes through an opening 104 in the lip 72 of the canopy and through a corresponding opening (not shown) in the canopy extension inner wall 83.

The light source 100 may be mounted to the cheeseplate 30, as shown in FIG. 5, so that its weight is not supported by the canopy 50, or located elsewhere, such as above the ceiling. The light source 100 may also provide light to other fiber optic elements in the system 10, such as the lightheads 14, 16.

Assembly of the canopy extension 70 is readily achieved, preferably as follows. The canopy extension housing 73 is preferably formed from a resiliently flexible material and has a narrow slit 106 in its inner and outer walls, as illustrated in FIG. 5. By grasping ends of the canopy extension housing 73 adjacent to the slit 106, the canopy extension can be pulled into a C-shape, allowing the light emitting component 60, comprising woven fiber optic element 68, to be fed into the cavity 86. The light pipe 102 passes through a suitably sized hole (not shown) in the inner wall 83 of the canopy extension 70. After installing the light emitting component 60 in the cavity 86, the canopy extension housing 73 is allowed to return to its original annular shape and the gasket 87 is fitted to the upper end 76 of the housing 73 to form the canopy extension 70. This latter step may be carried out before or after positioning the canopy extension housing 73 around the canopy 50.

When it is desired to fit the canopy extension 70 to the canopy 50, the light pipe 102 is fed through the hole 104 in the canopy and the hooks 75 are mounted to the lip 72 of the canopy. A free end of the light pipe 102 has a suitable connector which allows it to be snap fit into a corresponding connector on a housing for the light source 100, thereby bringing the free end of the light pipe 102 into alignment with the light source 100. It will be appreciated that where the light emitting component 60 includes a fluorescent tube, bank of LEDs, or other light emitting component which does not employ a separate light source 100, the light pipe is replaced with suitable electrical wiring for connecting the light emitting component with a source of power (not shown).

Figure 11:
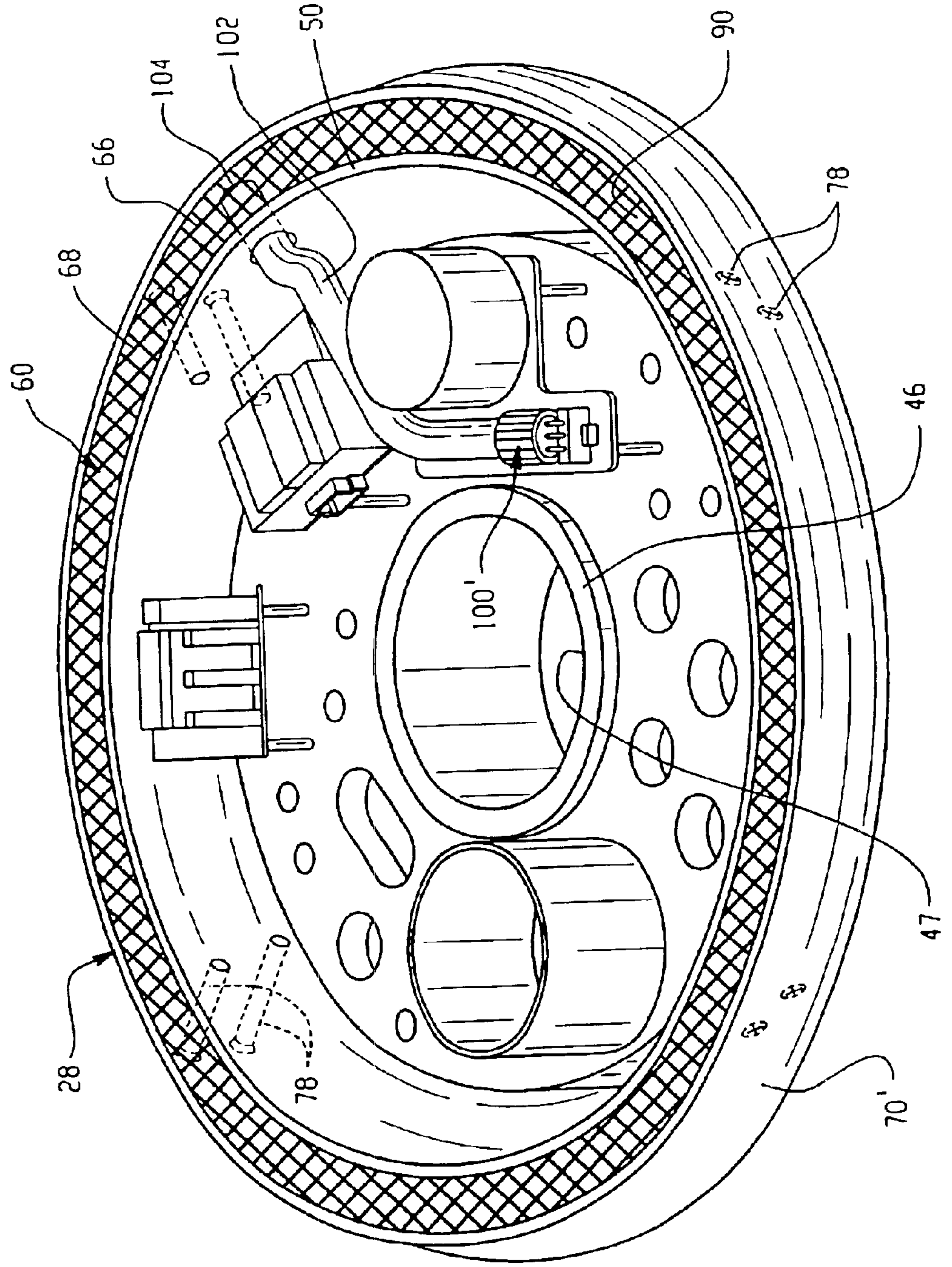
FIG. 11 is a perspective view of the canopy assembly of FIG. 7.
Figure 12:
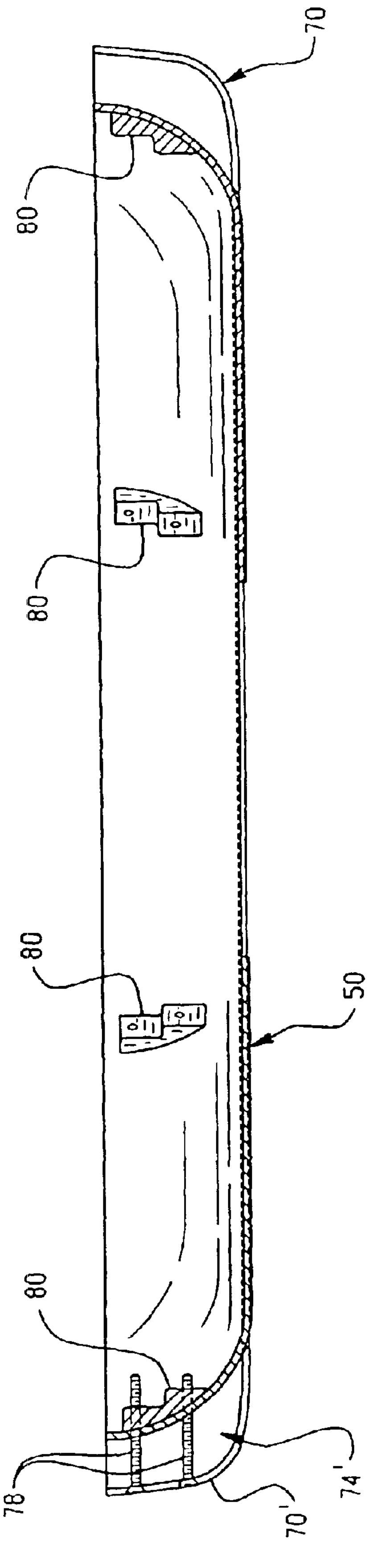
FIG. 12 is an enlarged sectional view of the canopy assembly of FIG. 7.

FIG. 11 shows a similar arrangement for the canopy extension 70'. In this embodiment, the woven fiber optic element 68 may be held in place in the socket 90 by suitable fixing members (not shown) so that it does not fall out during installation. The light pipe is fed through the hole 104 in the canopy, as for the embodiment of FIG. 5, and its free end snap fitted into position adjacent the light source 100. The bolts 78 are then inserted into the canopy and tightened until the canopy extension 70' is firmly attached to the canopy.

The ambient light 28 thus provides a centrally located lighting system, which illuminates the operating room uniformly. It avoids direct and harsh lighting, and reduces the chance of adversely affecting the vision of personnel in the operating room. The lightheads need not be moved when ambient light is needed. Although a woven fiber optic panel 68 provides relatively uniform light, the canopy extension 70, 70' optionally utilizes well known light softening techniques, such as frosting, to soften and homogenize the light, allowing more uniform light to emanate into the operating room while softening any direct bright spots.

In operation, the surgeon or other operating room staff member switches on one or more of the lightheads 14, 16 using a switch 120, which may be mounted on the lighthead, as shown in FIG. 1, or located on a wall of the operating room. Multiple switches may be provided for each lighthead, allowing both the surgeon and non-sterile personnel to operate the lightheads. Each lighthead includes a light source or light emitting component 122, such as a bulb, fluorescent tube, or fiberoptic light source. When the surgeon desires more uniform illumination of the room, the lightheads are generally switched off, or reduced to a low level of illumination, using the switch 120. The same switch 120 may be used to control the ambient light 28, such that the ambient light comes on when the lighthead light sources are switched off.

Where an ambient light 28 is to be retrofitted to an existing system, the light emitting component 60 is mounted to the canopy extension 70, 70' and the extension fitted to the canopy 50. Electrical connections to a source of power are made, as appropriate. If a separate light source 100 is used, this is mounted to the cheeseplate 30 and a suitable hole 104 drilled in the canopy for receiving the light pipe 102 therethrough.

The invention has been described with reference to the preferred embodiments obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A lighting system comprising:

a mounting system;

a lighthead including a first light emitting component;

an arm assembly adapted to support the lighthead in a selected position relative to the mounting system;

a canopy assembly, mounted to the mounting system;

an ambient light including:

a second light emitting component including a fiberoptic mesh, the second light emitting component being carried by the canopy assembly;

a light source; and at least one light pipe adapted to couple the light source with the fiberoptic mesh.

2. The lighting system of claim 1, wherein the second light emitting component is substantially annular and is at least partly enclosed by a removable peripheral wall of the canopy assembly.

3. The lighting system of claim 1, wherein the canopy assembly includes a canopy main body and a light transmissive canopy extension, mounted to the canopy main body, the canopy extension supporting the second light emitting component.

4. The lighting system of claim 3, wherein the canopy extension is annular and has an outer diameter which is larger than an outer diameter of the canopy main body.

5. The lighting system of claim 3, wherein the canopy extension is formed in at least two sections which together define an annulus.

6. The lighting system of claim 3, wherein the canopy extension defines an enclosed pocket adapted to receive the second light emitting component therein.

7. The lighting system of claim 3, wherein the canopy extension and canopy main body define a socket therebetween adapted to receive the second light emitting component.

8. The lighting system of claim 1, wherein the second light emitting component has an annular shape.

9. The lighting system of claim 1, wherein the light source is a right generating element selected from the group consisting of fluorescent tubes, light emitting diodes, incandescent bulbs, discharge lights, and fiberoptic elements.

10. The lighting system of claim 9, wherein the second light emitting component includes a circular fluorescent tube.

11. The lighting system of claim 9, wherein the second light emitting component includes a circular array of fluorescent tubes.

12. The lighting system of claim 9, wherein the first light emitting component is a light generating element selected from the group consisting of fluorescent tubes, light emitting diodes, incandescent bulbs, discharge lights, and fiberoptic elements.

13. The lighting system of claim 1, wherein the first light emitting component is a light generating element selected from the group consisting of fluorescent tubes, light emitting diodes, incandescent bulbs, discharge lights, and fiberoptic elements.

14. The lighting system of claim 1, further comprising a switch associated with the lighthead, the switch selectively operating the first light emitting component and the second light emitting component.

15. The lighting system of claim 1, wherein the mounting system includes:

a tube, the arm assembly being rotatably mounted to a lower end of the tube, the canopy assembly being mounted to the tube by a clamp ring; and a cheeseplate defining an aperture adapted to receive the tube therethrough.

16. A medical device suspension system comprising:

a support hub;

an arm assembly mounted for rotational movement relative to the support hub by a spindle, the arm assembly supporting an associated medical device at a distal end thereof;

a canopy assembly mounted to the support hub and extending from the hub above the spindle, the canopy assembly defining an outer peripheral edge; and an ambient light including:

a fiberoptic mesh;

a light source; and a light pipe coupling the light source with the fiberoptic mesh.

17. The medical device suspension system of claim 16 wherein the canopy assembly includes:

a pocket or socket adjacent the peripheral edge which accommodates the light emitting component.

18. The medical device suspension system of claim 16, wherein the canopy assembly includes:

a canopy main body, which is mounted to the support hub; and a canopy extension, removably mounted to the canopy main body, which supports, at least in part, the light emitting component.

19. The medical device suspension system of claim 18, wherein the canopy extension and canopy main body define an upwardly open socket therebetween, adjacent the peripheral edge, which receives the light emitting component.

20. The medical device suspension system of claim 18, wherein the canopy extension includes an inner peripheral wall and an outer peripheral wall which define an enclosed pocket therebetween which accommodates the light emitting component.

21. The medical device suspension system of claim 16, wherein the medical device is an apparatus selected from the group consisting of lightheads, task lights, video monitors, and cameras.

22. A method of fitting an ambient light to a medical suspension system comprising:

providing an ambient light including a light source and a fiberoptic mesh coupled with the light source; and, mounting a canopy extension to a canopy of the suspension system, the canopy extension supporting, at least in part, the ambient light.

23. A lighting system comprising:

a mounting system;

a lighthead including a first light emitting component;

an arm assembly adapted to support the lighthead in selected positions relative to the mounting system; and, an ambient light supported relative to said mounting system for providing ambient light in an area adjacent said lighthead, the ambient light including an array of light emitting diodes on said arm assembly adjacent said mounting system.

24. A lighting system comprising:

a mounting system;

a lighthead including a first light emitting component;

an arm assembly adapted to support the lighthead in selected positions relative to the mounting system; and, an ambient light supported relative to said mounting system for providing ambient light in an area adjacent said lighthead, the ambient light including a canopy assembly supported relative to the mounting system, and an array of light emitting diodes arranged substantially in an annulus surrounding a portion of said arm assembly.

25. The lighting system of claim 24, wherein the canopy assembly includes a light transmissive member.

26. A lighting system comprising:

a mounting system;

a lighthead including a first light emitting component;

an arm assembly adapted to support the lighthead in a selected position relative to the mounting system; and, an ambient light supported relative to said mounting system for providing ambient light in an area adjacent said lighthead, the ambient light including a set of light emitting diodes carried on said mounting system adjacent said arm assembly.

* * * * *